(12) United States Patent
Siess et al.

(10) Patent No.: US 8,025,647 B2
(45) Date of Patent: Sep. 27, 2011

(54) INTRODUCTION DEVICE FOR INTRODUCING AN OBJECT INTO A VESSEL OF A BODY

(75) Inventors: Thorsten Siess, Wuerselen-Bardenberg (DE); Josef Penners, Juelich (DE)

(73) Assignee: Impella Cardiosystems GmbH, Aachen (DE)

( * ) Notice: Subject to any disclaimer, the term of this patent is extended or adjusted under 35 U.S.C. 154(b) by 1197 days.

(21) Appl. No.: 10/549,385

(22) PCT Filed: Mar. 11, 2004

(86) PCT No.: PCT/EP2004/002487
§ 371 (c)(1),
(2), (4) Date: Jun. 30, 2006

(87) PCT Pub. No.: WO2004/082755
PCT Pub. Date: Sep. 30, 2004

(65) Prior Publication Data
US 2006/0271085 A1 Nov. 30, 2006

(30) Foreign Application Priority Data
Mar. 21, 2003 (DE) .............................. 203 04 533 U

(51) Int. Cl.
*A61M 5/00* (2006.01)

(52) U.S. Cl. ......... 604/264; 604/158; 606/108; 606/191
(58) Field of Classification Search ............... 604/93.01, 604/21, 158, 164.01, 164.04, 164.06, 164.07, 604/164.12, 170.01, 170.12, 264, 272, 523, 604/533; 606/191, 108
See application file for complete search history.

(56) References Cited

U.S. PATENT DOCUMENTS
2004/0044266 A1 * 3/2004 Siess et al. ...................... 600/16

FOREIGN PATENT DOCUMENTS
| DE | 91 08 043.6 | 10/1991 |
|----|-------------|---------|
| EP | 0596 172 A2 | 12/1992 |
| WO | WO 02/43791 A1 | 6/2002 |

* cited by examiner

*Primary Examiner* — Nicholas D Lucchesi
*Assistant Examiner* — Quynh-Nhu H Vu
(74) *Attorney, Agent, or Firm* — Fulwider Patton LLP; Gunther O. Hanke, Esq.

(57) ABSTRACT

An introduction device for introducing an object into a vessel of a body comprises a tubular channel (15) and a dilator (11) carrying the channel. To keep the diameter of the body canal as small as possible, the wall thickness of the channel (15) is max. 0.06 mm. The channel (15) is made of a hard plastic material, such as polyamide or polyester, such that the channel (15) is not deformed by compression when the device is advanced in the body and the dilator (11) is retracted. Further, a tight fit on the dilator also prevents such compressions.

8 Claims, 2 Drawing Sheets

INTRODUCTION DEVICE FOR INTRODUCING AN OBJECT INTO A VESSEL OF A BODY

Figure 1:
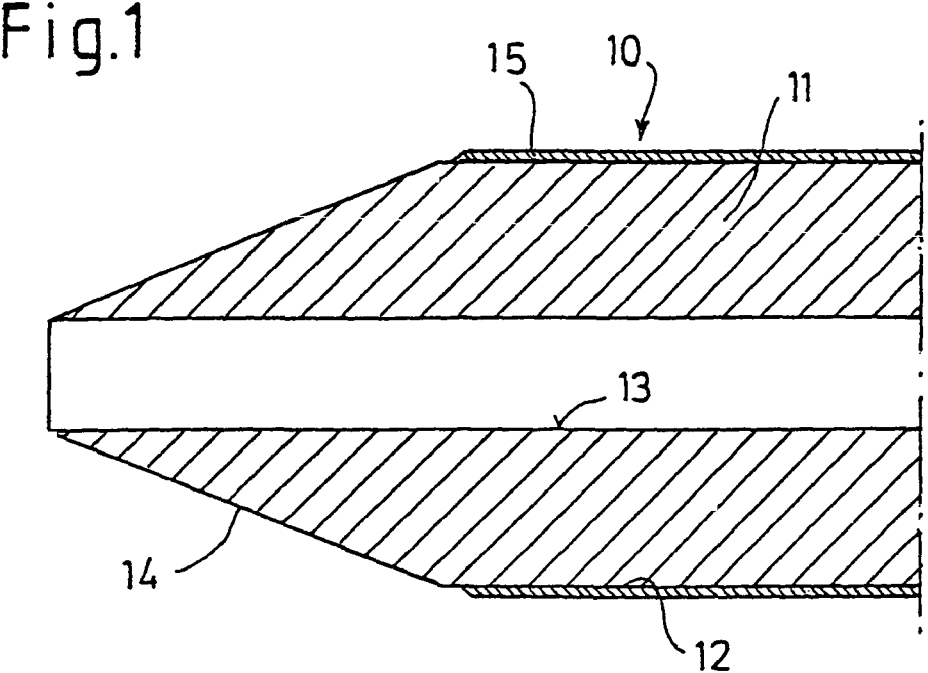

The invention relates to an introduction device for introducing an object into a vessel of a body, comprising a tubular channel and a dilator carrying the channel, wherein the dilator comprises a conical tip portion and is adapted to be retracted form the channel.

Such an introduction device is described in WO 02/43791 A1 (Impella). The introduction device may, for example, be used for advancing an intravascular pump through a blood vessel. In this manner, a blood pump can be introduced into a blood vessel of the body and advanced therein up to a desired location. The channel is composed of a relatively rigid tube provided with a haemostatic valve at the proximal end (averted from the patient). The channel is slid onto a dilator. A guide wire extends through the dilator, which is inserted through the skin into the blood vessel using the Seldinger technique. The dilator, together with the channel placed thereupon, is advanced over the guide wire, wherein the conical tip portion of the dilator expands (dilates) the narrow canal extending through the body tissue. When the dilator has reached the blood vessel and the channel has been advanced to its final position in the blood vessel, the dilator is retracted from the channel. After removal of the dilator, which has temporarily straightened the channel and the vessel area, the channel describes a curve corresponding to the respective anatomy. This involves the risk that the channel kinks or the circular cross-section is deformed by the bend into an oval shape, and consequently the channel is blocked towards the object to be introduced. A deformed thick-walled channel can only be caused to reestablish the desired circular cross-section of the channel by application of large axial forces as can be introduced by a dilator.

If instead of the dilator the catheter to be introduced is used, which may comprise, for example, an intravascular blood pump, the forces to be applied axially and radially are reduced and do possibly not suffice to remedy the deformation of the thick-walled channel.

At a relatively large inner diameter of the channel of 12 F (F=French) corresponding to 4 mm, the outer diameter of the channel resting on the dilator becomes very large, namely approximately 14-15 F, because of the wall thickness of the channel. The larger the diameter of the body canal through which the channel extends, the higher is the risk that blood flows out after removal of the channel. On the other hand, the channel must have a certain degree of rigidity such that it does not fold like an accordion on the dilator during the introduction process. During removal of the dilator there is also the risk that the channel folds in an accordion-like manner.

It is an object of the invention to provide an introduction device for relatively large objects, wherein the body canal to be produced has a diameter as small as possible.

According to the invention, this object is achieved with the features of claim 1. Accordingly, the channel has a wall thickness of max. 0.06 mm and is made of a hard plastic material.

A hard plastic material comprises hard and tough plastic materials, such as polyamide and polyester. The channel has an extremely small wall thickness of max. 0.06 mm, and in particular of max. 0.03 mm. At an internal diameter of the channel of 4 mm, the outer diameter is only slightly larger. Thus the diameter of the body canal to be produced, through which the channel extends, becomes as small as possible.

Preferably, prior to sliding the channel onto the dilator, the inner diameter of the channel is at least as large as the outer diameter of the dilator. This means that both diameters are identical with a tolerance of a hundredth millimeter such that the channel forms an interference fit on the dilator. It may further be intended that the channel forms a force fit on the dilator. Here, the inner diameter of the channel is slightly smaller than the outer diameter of the dilator. The tight fit ensures that there is no gap between the dilator and the channel. Further, the accordion-like folding (scalation) of the channel during the advance movement through the body tissue and retraction of the dilator is prevented. In particular the feature of the hard plastic material, which is not radially expandable, prevents scalation.

According to a preferred embodiment of the invention, to facilitate retraction of the dilator from the channel, the dilator and/or the channel comprise a low-friction slip material. For example, the dilator or the channel may be provided with a Teflon coating. In any case, the material pairing of the channel and the dilator should have a small friction coefficient $\mu$ in the contact area. For this purpose, the dilator may further be wetted with a slip agent.

According to a preferred aspect of the invention, a connecting device for injecting a pressurized fluid into the channel is provided. The connecting device is located at the proximal end of the channel (distal to the patient). The connecting device can be connected to a pressure source for injecting a pressurized medium into the channel such that the channel is slightly lifted off the dilator. The channel is lifted off only to a very small degree to allow the channel to slide on the thin fluid film. The degree of lift-off is much smaller than the wall thickness of the channel and in particular smaller than 5% of the wall thickness.

According to a preferred aspect of the invention, which forms however also an independent aspect, the channel comprises a distal end section which at least partly overlaps the conical tip portion of the dilator. The distal end section causes the channel to be entrained when the dilator is advanced, and prevents an accordion-like folding of the channel when the latter is pushed through the closely fitting body tissue which is to be expanded. In this embodiment, a small annular gap may exist between the dilator and the channel, with a gap width of max. 0.2 mm. During retraction of the dilator the channel is prevented from folding.

The end section of the channel may be defined towards the remaining portion of the channel by a tear-off line. Here, the end section is preferably adhesively bonded to the tip portion of the dilator. Since the dilator, which is at first located in the channel, causes the tissue and the vessels to straighten, there is the risk, after removal of the dilator, that the channel conforms to the anatomical curves. Consequently, curves may exist which automatically cause a very thin-walled channel to kink.

However, in contrast to thick-walled channels, these kinks can be easily straightened by the catheter to be introduced, since here extremely small wall thicknesses are involved. It is however a precondition that the catheter to be introduced comprises a round (spherical) tip. Thus the thin wall can be prevented from being penetrated when the kinked channel is straightened. The channel thus acts as a guide, and any kink occurring in the channel can be temporarily remedied until the catheter has passed through the channel.

Figure 2:
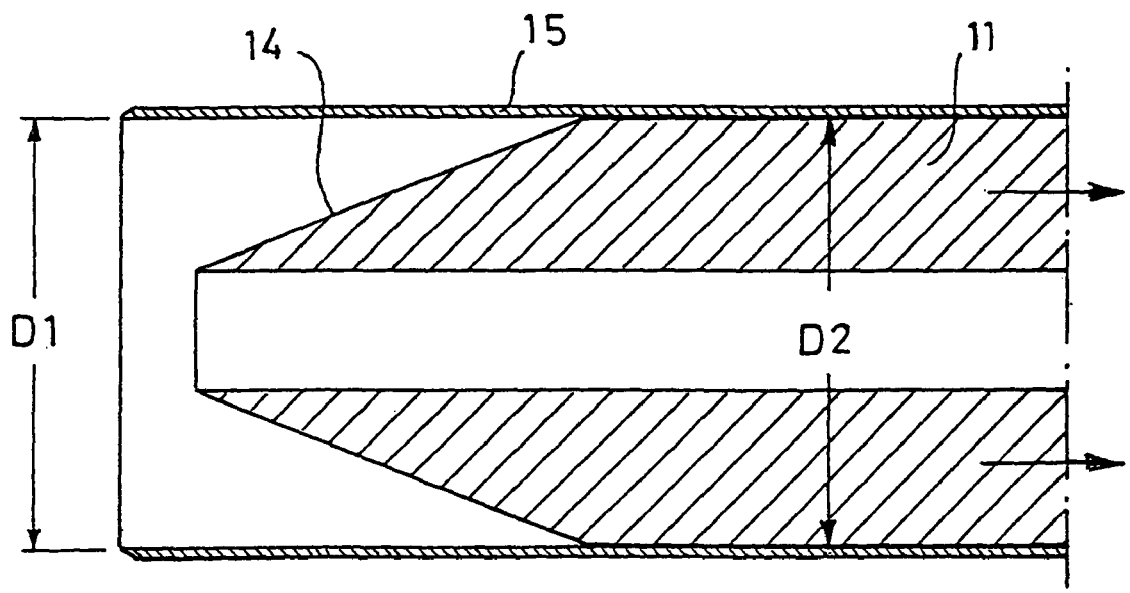
Figure 3:
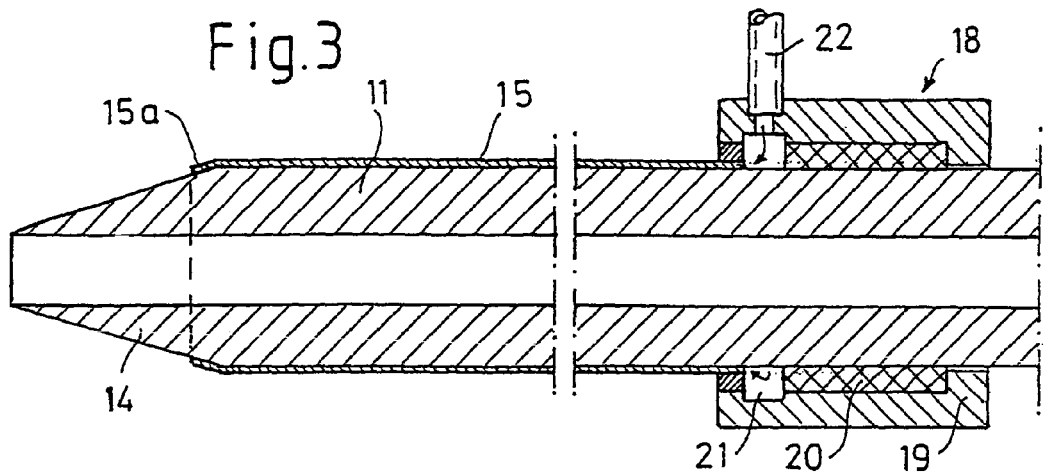
Figure 4:
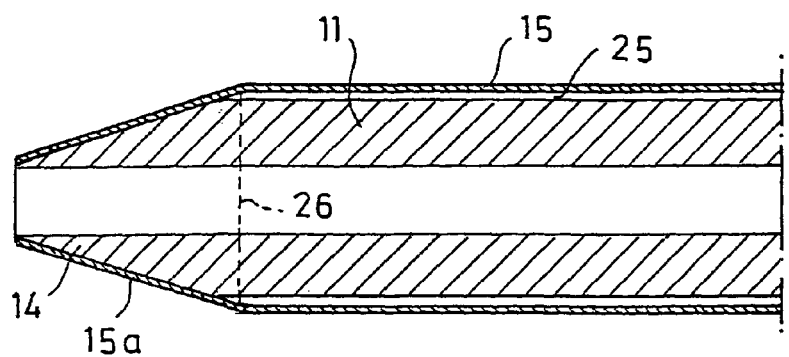
Figure 5:
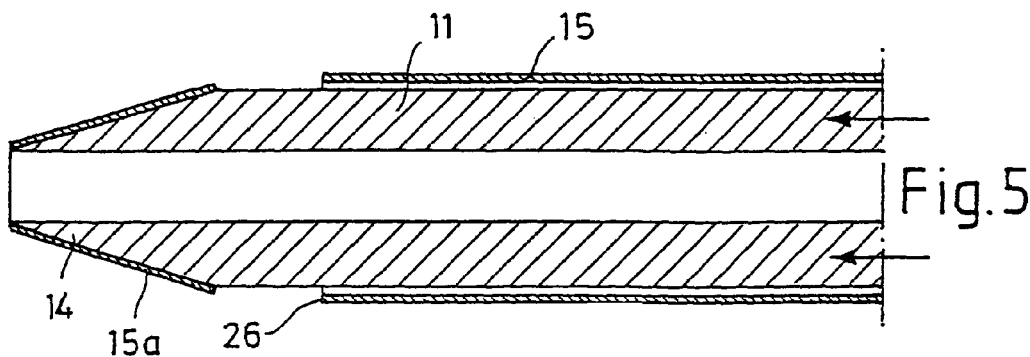
Figure 6:
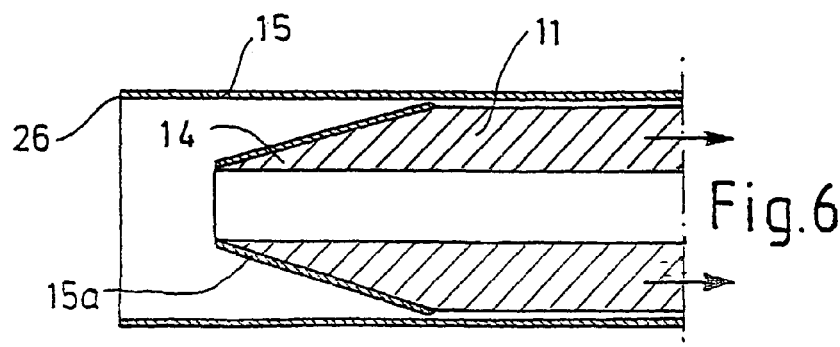

Hereunder embodiments of the invention are explained in detail with reference to the drawings in which:

FIG. 1 shows a longitudinal section of the distal end of the introduction device, FIG. 2 shows the introduction device during retraction of the dilator, FIG. 3 shows a schematic longitudinal section of the overall introduction device comprising a connecting device at the proximal end, FIG. 4 shows another embodiment with an annular gap between the dilator and the channel, FIG. 5 shows a temporary advance movement of the dilator for tearing off the tip portion of the channel, and FIG. 6 shows retraction of the dilator in the channel.

The introduction device is generally configured and used as described in WO 02/43791 A1. The channel is preferably used for introducing an intravascular blood pump into a blood vessel. The blood pump, which comprises a drive portion and a pump portion, has generally a cylindrical shape and an outer diameter of less than 4 mm.

The introduction device 10 for introducing an object, e.g. a blood pump, into a body vessel comprises an elongate dilator 11 composed of a straight shaft with a cylindrical smooth surface 12. Through the dilator 11 a central canal 13 extends through which a guide wire (not shown) is adapted to pass. The dilator 11 is slid onto the guide wire. At its distal end the dilator 11 comprises a conical tip portion 14 with the aid of which the dilator 11 expands the body tissue and dilates the thus produced body canal during the advance movement. The dilator 11 is made of a rigid plastic material. Its wall thickness is so large that no substantial deformations can occur. Deflections are possible, but kinks are practically impossible.

The channel 15 is slid onto the dilator 11. The channel is composed of a tubular shell with a wall thickness of max. 0.06 mm, preferably max. 0.04 mm, and in particular approximately 0.03 mm. The material of the channel 15 is a hard plastic material, such as polyamide or polyester. The channel 15 forms a force fit on the dilator 11. This means that the inner diameter D1 of the channel 15 is slightly smaller than the outer diameter D2 of the dilator 11 (FIG. 2).

When the dilator is introduced into the body of the patient, the distal end of the channel 15 is located behind the tip portion 14. When the distal end of the channel 15 is located in the blood vessel, the dilator 11 is retracted, as shown in FIG. 2, wherein the channel 15 is retained and remains in situ in the body. The channel can be repositioned only when the dilator is introduced again.

The peripheral surface 12 of the dilator 11 may be provided with a low-friction coating, e.g. of Teflon or a hydrophilic thin film.

Due to the material hardness of the channel 15 and due to the tight fit of the channel on the dilator 11 there is no risk of folding during the passage through the skin or in the collagenic structures of the vessels in the tissue since the channel 15 can evade neither towards the inside nor towards the outside.

FIG. 3 shows an embodiment wherein the channel 15 comprises a distal end section 15a which partly overlaps the conical tip portion 14 of the dilator. The end section 15a forms a channel sleeve extending towards the inside, whereby the channel 15 is secured against being pushed back on the dilator 11.

As shown in FIG. 3, at the proximal end of the channel 15 a connecting device 18 is arranged which is illustrated only schematically here. The connecting device 18 comprises a housing 19 which sealingly surrounds the rear end of the channel 15 and allows the dilator 11 to pass through. The housing 19 contains a haemostatic valve 20 which isolates the canal extending through the channel 15 when the dilator 11 has been retracted, whereby blood is prevented from issuing.

Further, the connecting device 18 contains, in the housing 19, an annular canal 21 which is connected with a supply tube 22 through which pressurized fluid can be supplied. The pressurized fluid is fed from the annular canal 21 to the rear end of the channel and acts as a slip agent which allows the dilator 11 in the channel 15 to be retracted.

In the embodiment shown in FIG. 3 the channel 15 forms a force fit on the dilator 11 and is slightly expanded by the action of the pressurized fluid such that the channel 15 is lifted off and a thin low-friction fluid film is formed between the channel and the dilator.

FIGS. 1-4 show an embodiment wherein the inner diameter of the channel 15 is slightly larger than the outer diameter of the dilator 11. For example, the outer diameter of the dilator 11 is 12 F (4.0 mm) and the inner diameter of the channel 15 is 13 F (4.33 mm). The annular gap 25 allows low-friction retraction of the dilator 11. In this embodiment, too, the wall thickness of the channel is max. 0.06 mm.

The channel 15 comprises, at its proximal end, a conical tip portion 14 which is adhered to the conical tip portion 14, e.g. by an adhesive. The end section 15a is connected with the cylindrical portion of the channel 15 by a circumferential tear-off line 26, for example a perforation line or any other weakening line.

In the configuration shown in FIG. 4 the dilator 11 and the channel 15 are introduced over a guide wire into the body. When the channel 15 has entered the blood vessel, the dilator 11 first continues to advance, as shown in FIG. 5, such that the end section 15a is torn off the channel 15 at the tear-off line 26. The end section 15a remains on the dilator 11 which is subsequently retracted, as shown in FIG. 6, while the channel 15 remains in situ.

The invention claimed is:

1. An introduction device for introducing an object into a vessel of a body, comprising:
   a tubular channel and a dilator carrying the channel, wherein the dilator comprises a conical tip portion and is adapted to be retracted from the channel, wherein the channel has a wall thickness not larger than 0.06 mm and is formed exclusively of a hard plastic material.

2. The introduction device according to claim 1, wherein the inner diameter (D1) of the channel is at least as large as the outer diameter (D2) of the dilator prior to sliding the channel onto the dilator.

3. The introduction device according to claim 2, wherein the channel forms a force fit on the dilator.

4. The introduction device according to claim 1, wherein the dilator and/or the channel comprise a low-friction slip material.

5. The introduction device according to claim 1, further comprising a connecting device for injecting a pressurized fluid into the channel.

6. The introduction device, according to claim 1, wherein the channel comprises a distal end section which at least partly overlaps the conical tip portion.

7. The introduction device according to claim 6, wherein the end section is defined by a tear-off line.

8. The introduction device according to claim 1, wherein the end section of the channel is adhesively bonded to the tip portion of the dilator.

* * * * *